United States Patent
Shepard et al.

(10) Patent No.: US 9,831,283 B2
(45) Date of Patent: Nov. 28, 2017

(54) SYSTEMS AND METHODS FOR IMAGING USING SINGLE PHOTON AVALANCHE DIODES

(71) Applicant: The Trustees of Columbia University in the City of New York, New York, NY (US)

(72) Inventors: Kenneth L. Shepard, Ossining, NY (US); Ryan Michael Field, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 626 days.

(21) Appl. No.: 14/247,983

(22) Filed: Apr. 8, 2014

(65) Prior Publication Data

US 2014/0217264 A1    Aug. 7, 2014

Related U.S. Application Data

(63) Continuation of application No. PCT/US2012/062716, filed on Oct. 31, 2012.

(60) Provisional application No. 61/554,311, filed on Nov. 1, 2011, provisional application No. 61/553,709, filed on Oct. 31, 2011.

(51) Int. Cl.
*H03F 3/08* (2006.01)
*H01L 27/146* (2006.01)
*G01N 21/64* (2006.01)
*H01L 31/107* (2006.01)

(52) U.S. Cl.
CPC ....... *H01L 27/14643* (2013.01); *G01N 21/64* (2013.01); *G01N 21/6408* (2013.01); *G01N 21/6458* (2013.01); *H01L 31/107* (2013.01); *H01L 31/1075* (2013.01); *G01N 2021/6441* (2013.01)

(58) Field of Classification Search
CPC ............... H01L 31/107; H01L 31/1075; H01L 27/14643; H01L 27/14645; G01N 21/6458; G01N 21/64
USPC ............ 250/208.1, 214.1; 356/5.01; 257/438
See application file for complete search history.

(56) References Cited

U.S. PATENT DOCUMENTS 6,342,701 B1    1/2002  Kash et al.
7,738,086 B2    6/2010  Shepard et al.
(Continued)

OTHER PUBLICATIONS

Giraud et al., "Fluorescence lifetime biosensing with DNA microarrays and a CMOS-SPAD imager", Biomedical Optics Express, 1(5):1302-1308 (Dec. 2010).

(Continued)

*Primary Examiner* — Thanh Luu
*Assistant Examiner* — Kevin Wyatt
(74) *Attorney, Agent, or Firm* — Baker Botts L.L.P.

(57) ABSTRACT

Single-photon avalanche diode includes a central junction having a central p+ area and a deep-n well in contact with the central p+ area, a p-type guard ring disposed between the central junction and the deep-n well, and a shallow trench isolation separated from the central p+ area. Imaging apparatus includes a plurality of pixels, each pixel comprising a complementary metal-oxide-semiconductor-implemented single photon avalanche device and one or more signal converters electrically coupled thereto and configured to detect changes in output therefrom.

22 Claims, 10 Drawing Sheets

An illustration diagram of SPAD design in standard 0.13-μm CMOS.

(56) References Cited

U.S. PATENT DOCUMENTS

| | | | |
|---|---|---|---|
| 2001/0020673 A1* | 9/2001 | Zappa | G01J 1/44 250/214 R |
| 2003/0189160 A1* | 10/2003 | Sakurai | H04N 9/045 250/208.1 |
| 2004/0073875 A1 | 4/2004 | Kitchin | |
| 2006/0192086 A1 | 8/2006 | Niclass et al. | |
| 2009/0315135 A1* | 12/2009 | Finkelstein | H01L 31/107 257/438 |
| 2010/0019295 A1* | 1/2010 | Henderson | H01L 31/107 257/292 |
| 2010/0078569 A1 | 4/2010 | Jarron et al. | |
| 2010/0133636 A1* | 6/2010 | Richardson | H01L 31/107 257/438 |
| 2010/0141769 A1* | 6/2010 | Kato | H04N 5/33 348/164 |
| 2010/0245809 A1* | 9/2010 | Andreou | H01L 31/107 356/222 |
| 2011/0089518 A1* | 4/2011 | Murshid | H01L 27/1446 257/448 |
| 2011/0180726 A1 | 7/2011 | Gratton et al. | |
| 2011/0206282 A1* | 8/2011 | Aisaka | G06T 11/60 382/195 |
| 2011/0249148 A1 | 10/2011 | Prescher et al. | |
| 2014/0246761 A1* | 9/2014 | Veeramma | H01L 29/8613 257/653 |
| 2016/0150963 A1* | 6/2016 | Roukes | A61B 5/6868 600/476 |

OTHER PUBLICATIONS

Kano et al., "Avalanche photodiode detection with object scanning and image restoration provides 2-4 fold resolution increase in two-photon fluorescence microscopy", Bioimaging, 4:187-197 (Nov. 1996).

Niclass et al., "A single photon avalanche diode implemented in 130-nm CMOS technology", IEEE Journal of Selected Topics in Quantum electronics, 13(4):863-869 (Jul.-Aug. 2007).

Patounakis et al., "Active CMOS array sensor for time-resolved fluorescence detection", IEEE Journal of Solid-State Circuits, 41(11):2521-2530 (Nov. 2006).

* cited by examiner

SYSTEMS AND METHODS FOR IMAGING USING SINGLE PHOTON AVALANCHE DIODES

CROSS REFERENCE TO RELATED APPLICATION

This application is a continuation of PCT/US12/062,716, filed Oct. 31, 2012, which claims priority to U.S. Provisional Patent Applications No. 61/554,311, filed Nov. 1, 2011, and No. 61/553,709, filed Oct. 31, 2011, each of which is incorporated by reference herein in its entirety.

STATEMENT REGARDING FEDERALLY SPONSORED RESEARCH

This invention was made with government support under Award No. R33-HG003089 awarded by the National Institute of Health. The government has certain rights in the invention.

BACKGROUND

Fluorescence lifetime imaging microscopy (FLIM) is an imaging technique that can utilize differences in the exponential decay rate of fluorescence from a fluorescent sample. A fluorophore can be excited by a photon and drop to the ground state with a certain probability based on the decay rates through a number of different decay pathways. The lifetime (decay rate) of the signal can be used to create an image, and allows for viewing of the contrast between materials with different fluorescence decay rates and materials that fluoresce at the same wavelength. Further utilizing two-photon microscopy can reduce the effect of photon scattering in thick layers of a sample, which can improve image quality. Some FLIM systems can utilize time-correlated single photon counting (TCSPC) instrumentation. Photomultiplier tubes (PMTs) and discrete time-to-digital converters (TDCs) can be used to implement TCSPC. These systems, however, can have limited speed with which FLIM images can be acquired, can be costly, large in size, and complex to implement.

Certain complementary metal-oxide-semiconductor (CMOS) processes can integrate a solid-state alternative to a PMT with timing electronics for on-chip TCSPC. These devices can be referred to as silicon photomultipliers (SiPMs) or, for TCSPC, single-photon avalanche diodes (SPADs), and can allow for arrays of detectors with improved frame rates through wide-field imaging. Detection limits for SPADs can be affected by noise, which can be in the form of the device's dark count rate (DCR). SPADs fabricated using certain processes have achieved DCRs as low as a few hundred Hz. However, certain SPADs in standard CMOS technology, which can have nodes smaller than 0.35 μm, can result in increased DCR or utilize specialized processes, such as hydrogen passivation, to reduce the DCR.

Fluorescence lifetime imaging microscopy (FLIM) can also be based on the differences in the exponential rate of decay of fluorescence from a sample. A fluorophore excited by a photon can drop to the ground state with a certain probability based on the decay rates through a number of different decay pathways. An image can then be composed using duration rather than intensity data of the signal.

Fluorescence lifetime can reveal changes in the local chemical and physical environment of a fluorophore, as well as the binding dynamics of single proteins through excited state interactions and Förster resonance energy transfer (FRET). Certain active dyes, molecular probes and even transgenic labeling strategies can utilize FRET to enable real-time observation of cellular processes both in vitro and in vivo. Certain metabolites, such as nicotinamide adenine dinucleotide (NADH) and flavin adenine dinucleotide (FAD), can also exhibit changes in their fluorescence lifetime during protein binding, which can be correlated with the health of the cell, with changes seen in precancerous cells and cells undergoing apoptosis and necrosis. While FRET can be detected using intensity-only measurements, quantitation can be impaired by experimental factors such as photobleaching and concentration dependent intensity fluctuations. Further, fluorescence lifetime imaging microscopy (FLIM) can be used for biological research, and can utilize time correlated single photon counting (TCSPC) instrumentation. A TCSPC detector can include photomultiplier tubes (PMTs), which can be large in size, and discrete time-to-digital converters (TDCs). FLIM microscopy can be implemented in a laser scanning configuration at a reduced complexity and cost by using only one TCSPC detector channel. However, dwell times of TCPSC channels can be on the order of 1 ms, and as such, a 128×128 pixel image can take over 16 seconds to acquire, which can prevent FLIM instrumentation from imaging real-time dynamic processes on millisecond time scales.

Accordingly, there is an opportunity for improved imaging systems.

SUMMARY

The disclosed subject matter provides techniques for imaging samples by fluorescence lifetime imaging microscopy, including by using low-noise single-photon avalanche diodes (SPADs). In an exemplary embodiment, a SPAD can include a p+/deep-n well diode having a shallow trench isolation area to separate devices. A photon passing through the depletion region of the SPAD can generate an electron-hole pair, which can lead to an avalanche breakdown and a corresponding reverse current spike. In one arrangement, the SPAD can further include an octagonal photosensitive area with a diagonal of 5 μm and a p-type guard ring to prevent edge breakdown.

The disclosed subject matter also provides methods of forming a single photon avalanche diode (SPAD). In an exemplary embodiment, a method includes limiting the presence of shallow trench isolation (STI) around a multiplication region defining a p+ implant region using a first mask layer, blocking an n+ implant using a second mask layer; and generating a p-type guard ring using a third mask layer. In some arrangements, the p-type guard ring can be configured to inhibit edge breakdown.

According to another exemplary embodiment, a method for operating a SPAD includes biasing the SPAD beyond its breakdown voltage ($V_{br}$) by an overvoltage ($V_{ov}$) without drawing current until a free carrier in the multiplication region triggers an avalanche. A higher $V_{ov}$ can produce an avalanche, and can thus increase sensitivity of the SPAD.

In some embodiments, multiple SPADs can be arranged in an array to create an imaging apparatus. Each SPAD in the apparatus can be connected in series with a quenching and resetting circuit. An active quenching circuit can reduce the voltage across the SPAD after an avalanche is triggered, which can minimize or halt the avalanche current. Thus, the current can be halted or minimized, and an active resetting circuit can digitally shorten the time between the triggering of an avalanche and the time when a new photon can be detected. Quenching can also reduce the incidence of afterpulsing—a noise event that can be caused by charges that do not clear the multiplication region before the diode is reset.

In some embodiments, the imaging apparatus can include multiple SPADs arranged in an array of pixels and coupled with a delay-locked loop-based time-to-digital converter (TDC). Each pixel can have an independent TDC and can thus detect a photon and record an arrival time during each FLIM measurement. Data obtained in this manner can be processed to generate an image.

The disclosed subject matter also provides for wide-field microscopy instruments. In an exemplary embodiment, an instrument can include an imaging apparatus of the type described herein. The imaging apparatus can be integrated on a printed circuit board coupled with a custom-made C-mount adapter. The instrument can provide for acquisition of images at improved rates as the number of beams scanning the tissue can be increased, which can allow for accumulation of fluorescence decay data for many pixels in parallel, and can thus produce images at the frame rate of the camera. Additionally, the imaging apparatus can be used in conjunction with a single laser beam expanded to cover a wide area of the sample.

DETAILED DESCRIPTION

The disclosed subject matter provides systems and methods for single photon avalanche diodes (SPADs). The disclosed subject matter can be used, for example, for an imaging apparatus utilizing one or more SPADs as disclosed herein. Additionally, the disclosed subject matter can be used for a variety of applications, for example and without limitation, wide-field microscopy, laser scanning microscopy, and/or endoscopy.

Figure 1A:
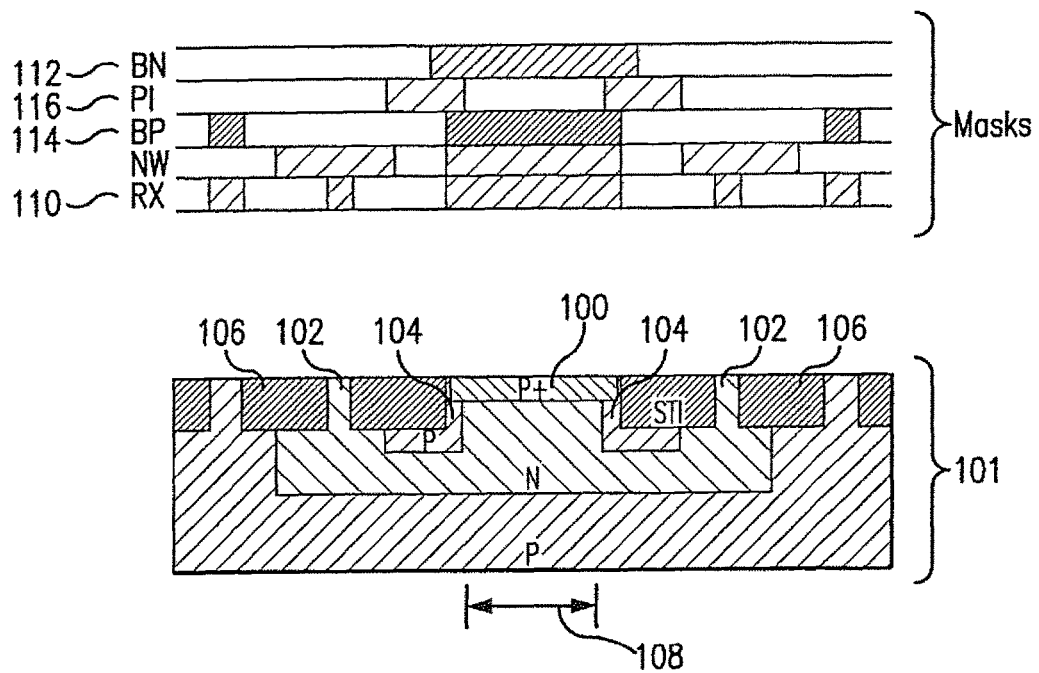
FIG. 1a is a diagram of an exemplary SPAD according to the disclosed subject matter
Figure 1B:
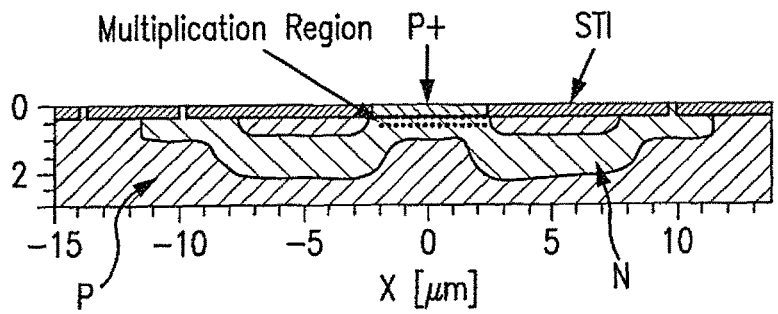
FIG. 1b is a diagram of an exemplary SPAD according to the disclosed subject matter.
Figure 1C:
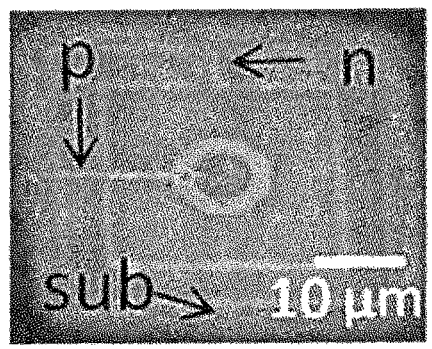
FIG. 1c is a micrograph of an exemplary SPAD according to the disclosed subject matter.

FIG. 1a shows a diagram illustrating an exemplary SPAD 101 according to the disclosed subject matter. A central p+ area 100 can be disposed adjacent to a deep-n well area 102, with a p-type guard ring 104 disposed between the p+ area 100 and the deep-n well 102, and a shallow trench isolation 106 (STI) separated from the central p+ area 100. FIG. 1b shows a completed, fabricated SPAD 101 which can have a photosensitive area 108. The photosensitive area 108, as embodied herein, can have an octagonal shape. Additionally or alternatively, the photosensitive area 108 can have a substantially round shape to avoid high electric fields at the corners, and thus prevent edge breakdown. An example of the fabricated SPAD 101 is shown in micrograph in FIG. 1c.

The SPAD 101 can be manufactured to allow for a low defect density, for example using Local Oxidation of Silicon (LOCOS) for field oxide growth, which can produce a higher quality Si/SiO interface compared to SPADs manufactured using shallow trench isolation (STI). Additionally, implants can allow for the inclusion of a p-type guard ring 104 around the sensor junction, which can prevent edge breakdown, and which can be utilized in addition to or in place of STI interfaces in the vicinity of the sensor junction.

FIG. 1a illustrates design masks that can be used to manufacture the SPAD 101. These masks can include, for example and without limitation, an active layer mask 110 (RX) that can define the location of the multiplication region, and can limit the presence of shallow trench isolation 106 (STI) around the multiplication region. A BN layer mask 112 can be used to define the p+ implant region, and a BP layer mask 114 can be used to block the n+ implants. A PI layer mask 116 can be used to generate a p-type guard ring 104 to prevent edge breakdown. As embodied herein, the SPAD can be configured, for example, to have a reverse bias breakdown voltage of −12.13 V and a multiplication region with a width of 115 nm at this bias voltage. However, alternative fabrication processes can be utilized and can produce different values.

Figure 2:
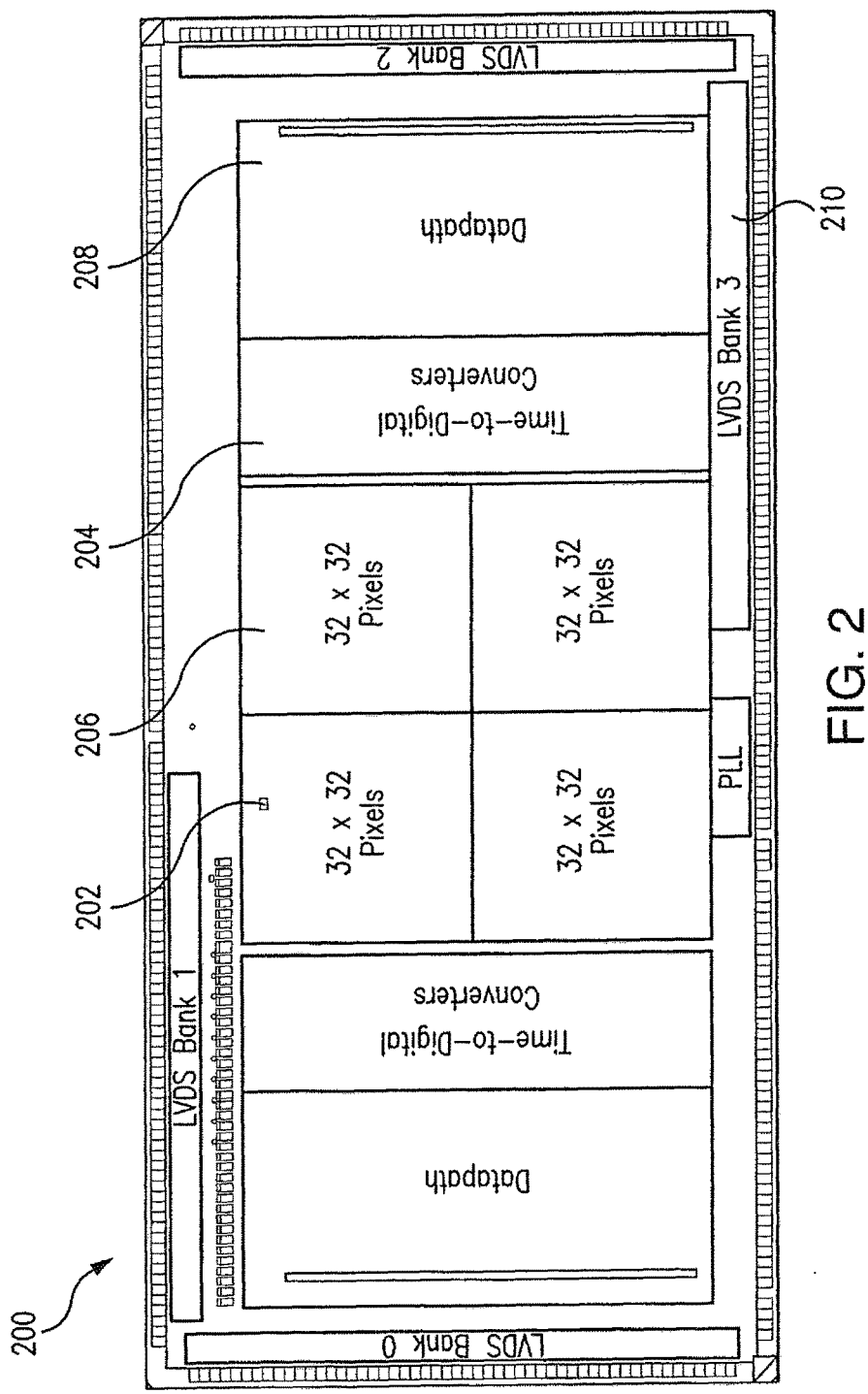
FIG. 2 is a diagram of an exemplary CMOS imaging apparatus according to the disclosed subject matter.

FIG. 2 illustrates an imaging apparatus 200 including the SPAD 101, embodied for example, and without limitation, in an array of pixels 202, with each pixel coupled to an independent time-to-digital converter (TDC) 204. Each TDC 204 can have a range and resolution configured for a particular application. For example and without limitation, biological fluorophores can have a range of 64 ns and a timing precision of 60 ps. As a photon enters the photosensitive area 108, it can trigger a so-called avalanche, causing a current to flow through the SPAD 101. In addition, each pixel can further be coupled to a quenching and resetting circuit 206 that can stop the avalanche and reset the SPAD 101, which can reduce noise and afterpulsing events. The TDC 204 can record the arrival time of the photon, and the datapath 208 can transmit the recorded arrival times for all activated pixels to the periphery, where they can be transmitted off chip over a Low-voltage differential signaling (LVDS) bus 210. A custom processor, for example and without limitation a programmable chip or an application-specific integrated circuit (ASIC), can perform an initial binning and/or histogramming operation on the photon arrival times, which can reduce the amount of data transmitted to a viewing computer using a high-speed PCIe interface.

The disclosed subject matter can provide imaging apparatus 200 with frame rates of 1 kHz or more with data compression techniques allowing data transfer rates of more than 40 Gbps, as described in more detail below. Certain maximum-likelihood-estimation techniques that can utilize parallelization, for example and without limitation matrix mathematics and fast iterative solvers, which can be assisted by on-chip hardware, can improve performance of the imaging apparatus 200.

In one embodiment, the SPAD 101 can be operated to perform photon counting in Geiger mode, that is biased beyond its breakdown voltage ($V_{br}$) by an overvoltage ($V_{ov}$). Geiger mode operation can include a quenching circuit, which can be a resistor in series with the diode. An avalanche can be triggered, and a current can flow through the resistor to cause a voltage drop. The voltage across the diode can thus rise above Vbr, which can halt the current, and the associated RC time constant can return to a reverse bias of (Vbr-Vov) to define a dead time for the SPAD. For example and without limitation, as embodied herein, a quenching resistance of 423 kΩ up to about 1 MΩ, can be used to yield avalanche current levels of 2.36 μA and a deadtime of 15 μs with Vov of 1.0 V. The quenching circuit can reduce the occurrence of afterpulsing, a noise event that can be caused by charges that do not clear the multiplication region before the SPAD is reset and retriggered. In some embodiments, a variable resistance, which can be implemented as a Positive-channel Field Effect Transistor (PFET), can tune the quenching resistance, and the active reset circuitry can reduce the RC time constant during the reset phase by switching a low resistance path in parallel with the quenching resistance.

For example and without limitation, and as embodied herein, the SPAD can have an exemplary photon detection probability of approximately 20%-29%, a dark count rate (DCR) of about 231 Hz-1 kHz and an impulse response of about 198 ps-250 ps.

Certain circuit capabilities can be used to provide a pixel capable of collecting multiple single-photon events per laser pulse, which can allow for accurate determination of the lifetime of a fluorophore in fewer laser repetitions and can allow for improved intensity excitation and image acquisition times while reducing pulse pileup. A masked maximum likelihood estimator (MLE) can allow for reconstruction of the exponential decay of a fluorophore by accounting for the deadtime of the detector. The log-likelihood formula for a standard Poisson point process can be represented as:

$$\mathcal{L}(\lambda) = \sum_{t=0}^{T} n_t \log(\lambda_t) - \lambda_t dt \qquad (1)$$

where n can represent the set of all observed data and λ can represent a parameter vector for the function that is most likely to produce the observations. Both a recorded photon event and the absence of such an event can contribute information to the estimator. However, due at least in part to the finite deadtime of the SPAD circuitry, there can be short periods of time following a photon event for which the arrival of a photon cannot be determined. As such, the data in n can be masked such that data during the deadtime of the detector is not considered, and the log-likelihood estimator can be represented as:

$$\mathcal{L}(\lambda) = \sum_{t=0}^{T} M_t [n_t \log(\lambda_t) - \lambda_t dt] \qquad (2)$$

where Mt can represent the mask. In order to design efficient circuits around the MLE processing technique, the log-likelihood equation can be further modified to:

$$\mathcal{L}(\lambda) = \sum_{t=1}^{T} [\log(\theta_t) E_t - \theta_t F_t dt] \qquad (3)$$

In this form, E and F can represent histograms of the masked photon events. E can represent a histogram of the arrival times of the photons, and F can represent a histogram of the unmasked time intervals. These two vectors can be recorded on-chip, through a set of counters, or off-chip, using a programmable chip, for example and without limitation, a Field Programmable Gate Array (FPGA) or an application-specific integrated circuit.

In addition to allowing for higher frame rate imaging with more intense excitation sources, the MLE technique described herein can reduce the data bandwidth utilized for FLIM. As an example, a 128×128 array with event-driven recording, 16-bit timing resolution (thermometer code, 4-bit encoded), six-bit coarse timing resolution (total of 24 bits/pixel/event), and the frame rate from simulation of up to 333 frames per second (150,000 repetitions/frame, 1% hit rate) can generate 19.6 Gbps. At a similar frame rate and array size, the MLE histogram technique can reduce the data generation to 11.6 Gbps or less. At a target frame rate of 1000 fps in MLE mode, a data rate of 35 Gbps can be supported with a 128-bit parallel channel, with each channel operating at less than 300 Mbps. In this manner, the MLE method can reduce the bandwidth requirement of the system and improve functionality.

Figure 3B:
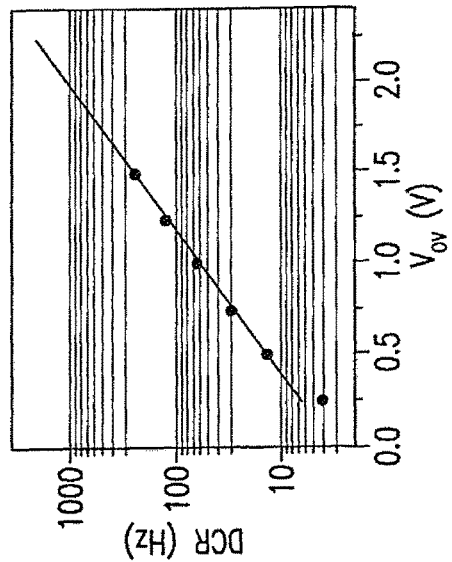
FIG. 3b is a diagram illustrating certain characteristics of the SPAD of FIG. 1.
Figure 3D:
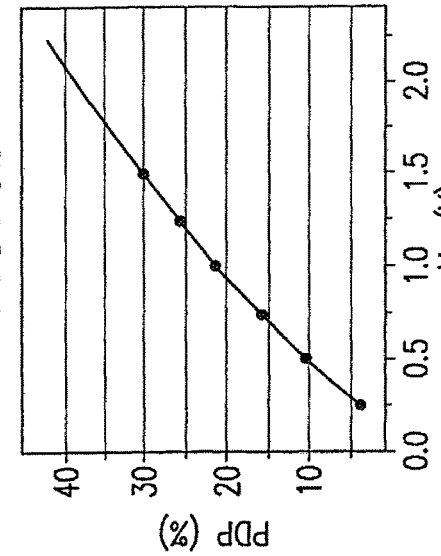
FIG. 3d is a diagram illustrating certain characteristics of the SPAD of FIG. 1.
Figure 3A:
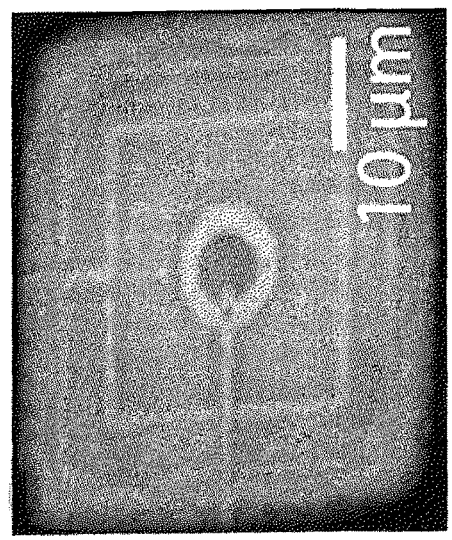
FIG. 3a is a micrograph of an exemplary SPAD according to the disclosed subject matter.
Figure 3C:
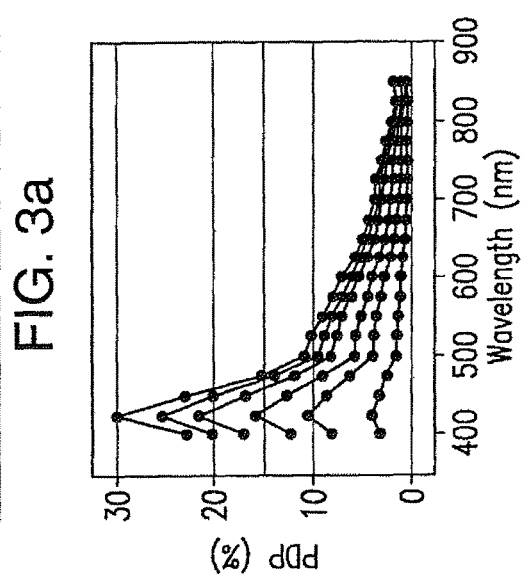
FIG. 3c is a diagram illustrating certain characteristics of the SPAD of FIG. 1.

FIG. 3(b) shows a graph of the dark count rate (DCR) as a function of the overvoltage (Vov) at room temperature, for a SPAD according to the disclosed subject matter. For a Vov of 0.25 V, the DCR is 6 Hz, increasing to only 231 Hz at 1.50 V. The DCR has the functional form A0eVov/Vo+Bo, where A0=3.06 s-1, B0=0.217 s-1, and Vov=0.347 V, for our device at room temperature. In FIG. 3(c), the photon detection probability (PDP) of this same device is shown as a function of photon wavelength for different values of Vov. The PDP peaks at 425 nm at just below 30% at a Vov of 1.50 V. While this peak is at a shorter wavelength than SPADs reported in other technologies, this can be explained by the shallow junction depths (~300 nm) that result from using the p+ mask for a PFET source and drain implant. In FIG. 2(d), we show the PDP as a function of Vov which has the functional form $A_0 e^{Vov/Vo} + B_o$, with p=0.759, A0=23.8 V-0.759 and Vc=0.156 V.

To further illustrate the performance of SPAD devices, and for purpose of comparison, an exemplary FLIM application in which a pulsed laser excites an ensemble of fluorophores with a monoexponential lifetime can be examined. The fluorescence emission from a single fluorophore as a nonhomogeneous Poisson point process can also be described. The PDP can be considered to be substantially constant in time, and the DCR can be represented as a Poisson process with a rate constant given by the experimentally measured DCR. The afterpulsing probability can be considered to be negligible, and the detector electronics arc can quench and reset the device in time for the next laser repetition. Three characteristic probabilities for the SPAD device can be determined: the probability of detecting an actual photon arrival, the probability of recording a miss when no photons are incident on the device, and the probability that a photon triggered an event given that an event has occurred. A figure of merit (FOM) can represent the product of these three probabilities, which can allow for selection of the SPAD device with the highest probability of properly recording photon events while avoiding noise events, and can be represented as:

FOM=P(detecting a hit|≥1 photon arrives)
  X P(detecting a miss|0 photons arrive)
  X P(photon hit|event occurred).

These probabilities can be determined analytically, consistent with the assumptions above, to yield:

$$FOM = \left\{1 + \frac{\exp[-(DCR \cdot T + \mu] - \exp[-(DCR \cdot T + \mu \cdot PDP)]}{1 - \exp(-\mu)}\right\} \quad (4)$$

$$\exp(-DCR \cdot T) \times$$

$$\left\{\frac{[1 - \exp(-\mu)] - \exp(-\mu \cdot PDP) \times \{1 - \exp[-\mu \cdot (1 - PDP)]\}}{[1 - \exp(-\mu)] - \exp(-\mu \cdot PDP) \times \{1 - \exp[-\mu \cdot (1 - PDP)]\} + [1 - \exp(-DCR \cdot T)]}\right\}$$

In this expression, T can represent the time window over which counts are recorded, which can be limited by the period of laser repetition, and μ can represent the integrated photon count over T, which can be determined by the intensity of the fluorescence being detected. In the range that μ<<1 and DCR·T<<1, the FOM can be represented as:

$$FOM = PDP \cdot \left(\frac{\mu \cdot PDP}{\mu \cdot PDP + DCR \cdot T}\right) \quad (5)$$

The incident photon rate can be determined by the monoexponential fluorescence decay, and thus $\mu = A \tau (1-e^{-T/\tau})$, where a can represent the greatest incident photon flux, and A can represent the SPAD device area. For T/τ>1, this becomes μ=A·a·T.

Figure 4:
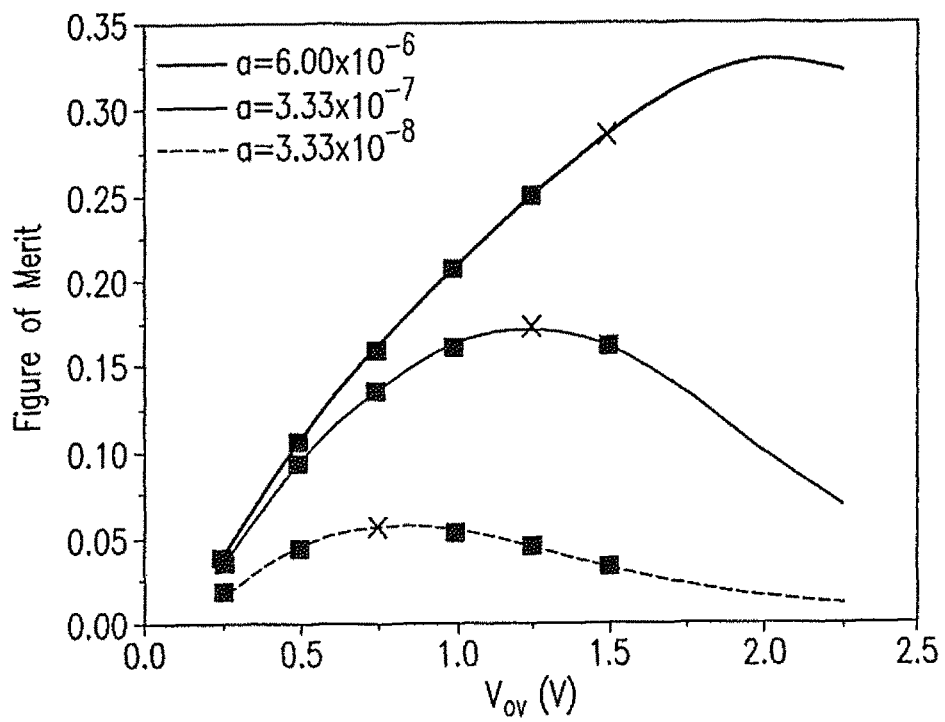
FIG. 4 is a diagram illustrating certain features of the SPAD of FIG. 1.

FIG. 4 shows the Figure of Merit as a function of $V_{ov}$ for a SPAD device for a=3.33×10$^{-8}$, 3.33×10$^{-7}$, and 6.00×10$^{-6}$ μm$^{-2}$ s$^{-1}$ with T=20 ns and r=3 ns, which can be representative of certain FLIM experiments. A bias point determined by the greatest FOM is shown in highlight for each curve. For purpose of comparison with other devices, the PDP and DCR for the SPAD device at the optimal $V_{ov}$ for a=6.00× 10$^{-6}$ μm$^{-2}$ s$^{-1}$ in FIG. 3 can be 1.5 V. Using similar representative T and r values, this value of a can result in no device in the comparison having a μ-PDP product such that a photon is detected in more than 1% of measurement windows, which can be consistent with reduced pulse pileup. The PDP and DCR given at certain bias points for other devices are also shown.

Figure 5:
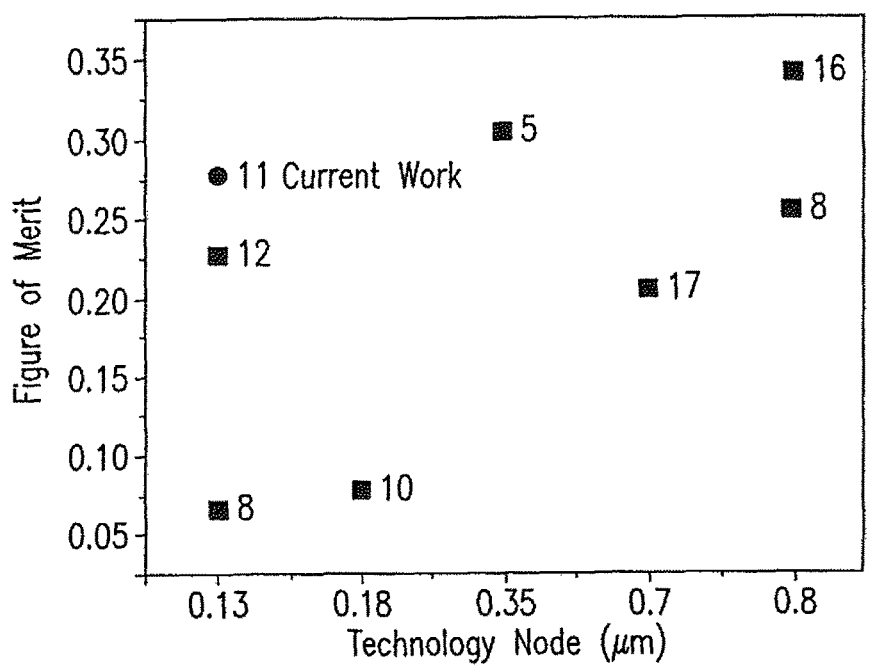
FIG. 5 is a diagram illustrating certain characteristics of the SPAD of FIG. 1.

FIG. 5 shows that devices in LOCOS technology nodes can out-perform the STI-based devices, due at least in part to their lower DCRs, and the SPAD device according to the disclosed subject matter is shown to have relatively high performance compared to devices implemented, as embodied herein, in 0.13 μm technology. In some applications, a relatively narrow impulse response can improve timing precision. The impulse response can be measured by exciting the SPAD with a 408 nm laser having a 45 ps full width at half maximum (FWHM) pulse and histogramming the resulting detector response with a Tektronix TDS7404 oscilloscope. The impulse response of measurement system, including the oscilloscope, laser, and SPAD can be 198 ps FWHM.

With integrated on-chip data processing, wide-field lifetime measurements in the form of a 128-by-128 pixel image can be achieved, at incident-photon-limited frame rates as high as 1 kHz, dark-count rates of less than 100 Hz and with simultaneously captured temporal-binning at time resolutions of less than 60 ps. This frame rate can be more than three orders of magnitude faster than can be achieved in certain commercial FLIM systems, such as systems based on laser scanning and PMTs or CCD imagers with gated intensifiers.

To implement a FLIM system, sensors made up of fabricated single-photon avalanche diodes (SPADs) as disclosed herein can be used. SPADs can have reduced noise and improved sensitivity compared to other sensor types, and can be used to create more compact imaging systems with improved image acquisition times.

In one embodiment, the SPADs disclosed herein can be used in a time-correlated single-photon counting (TCSPC) mode, in which photon arrival time histograms can be recorded through time-to-digital conversion of photon-activated pulses from the detectors. The SPADs can be further integrated into a complementary metal-oxide semiconductor (CMOS) process to create arrays of detectors, which can allow for higher frame rates with wide-field imaging. Such SPADs can be manufactured by repurposing design layers from established processes, which can be implemented with few or no manufacturing modifications, and thus can reduce manufacturing costs.

In one embodiment, a CMOS integrated circuit with low-noise single-photon avalanche diodes (SPADs) can be utilized for high-speed FLIM using time-correlated single-photon counting as shown in FIG. 2. In some embodiments, the CMOS integrated circuit can include a 64×64 array of pixels with low-noise SPADs, and each SPAD can be coupled to independent time-measurement circuitry as shown in FIG. 2. In an alternative embodiment, the CMOS integrated circuit can include an 128×128 array of pixels with low-noise SPADs, wherein each SPAD can be coupled to independent time-measurement circuitry as shown in FIG. 2. Each pixel can thus be equipped to detect incoming photon events, for one or multiple photons per laser pulse, and record an arrival time during each laser pulse of a FLIM measurement as shown in FIG. 7.

Figure 6:
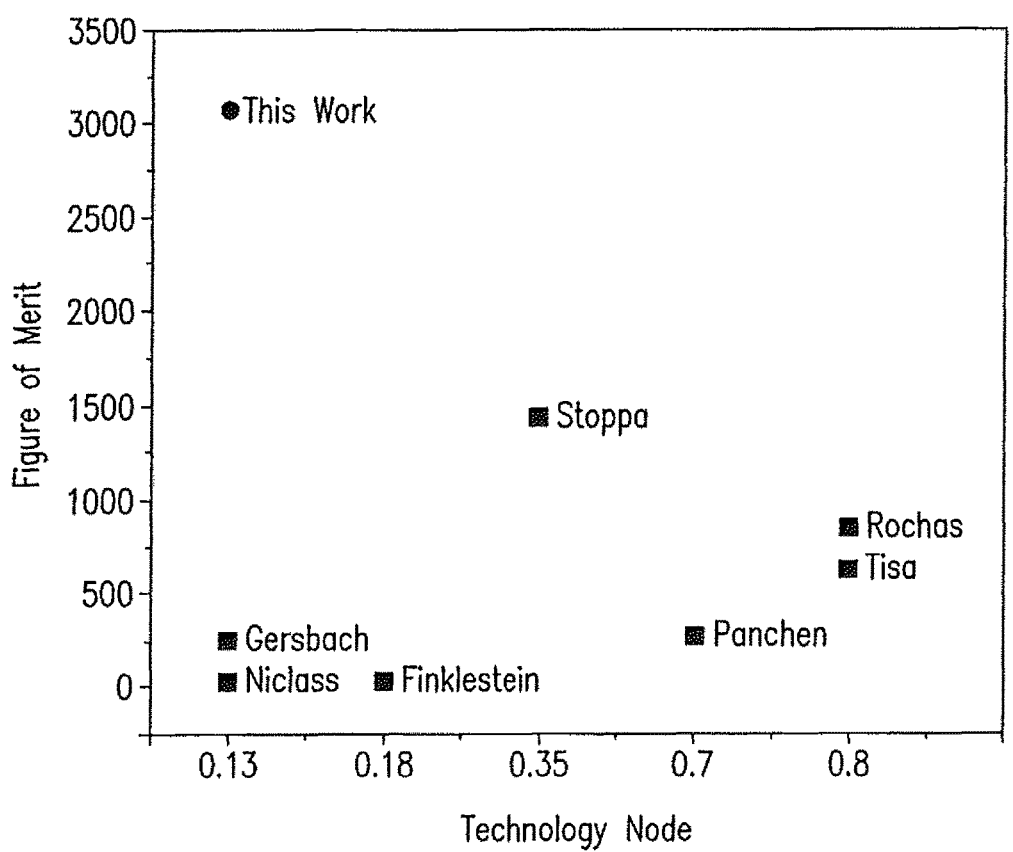
FIG. 6 is a diagram further illustrating certain characteristics of the SPAD of FIG. 1.

FIG. 6 shows a comparison between prior art SPADs systems and SPADs according to the presently disclosed subject matter using a Figure of Merit, for example as shown in eq. 5.

Figure 7:
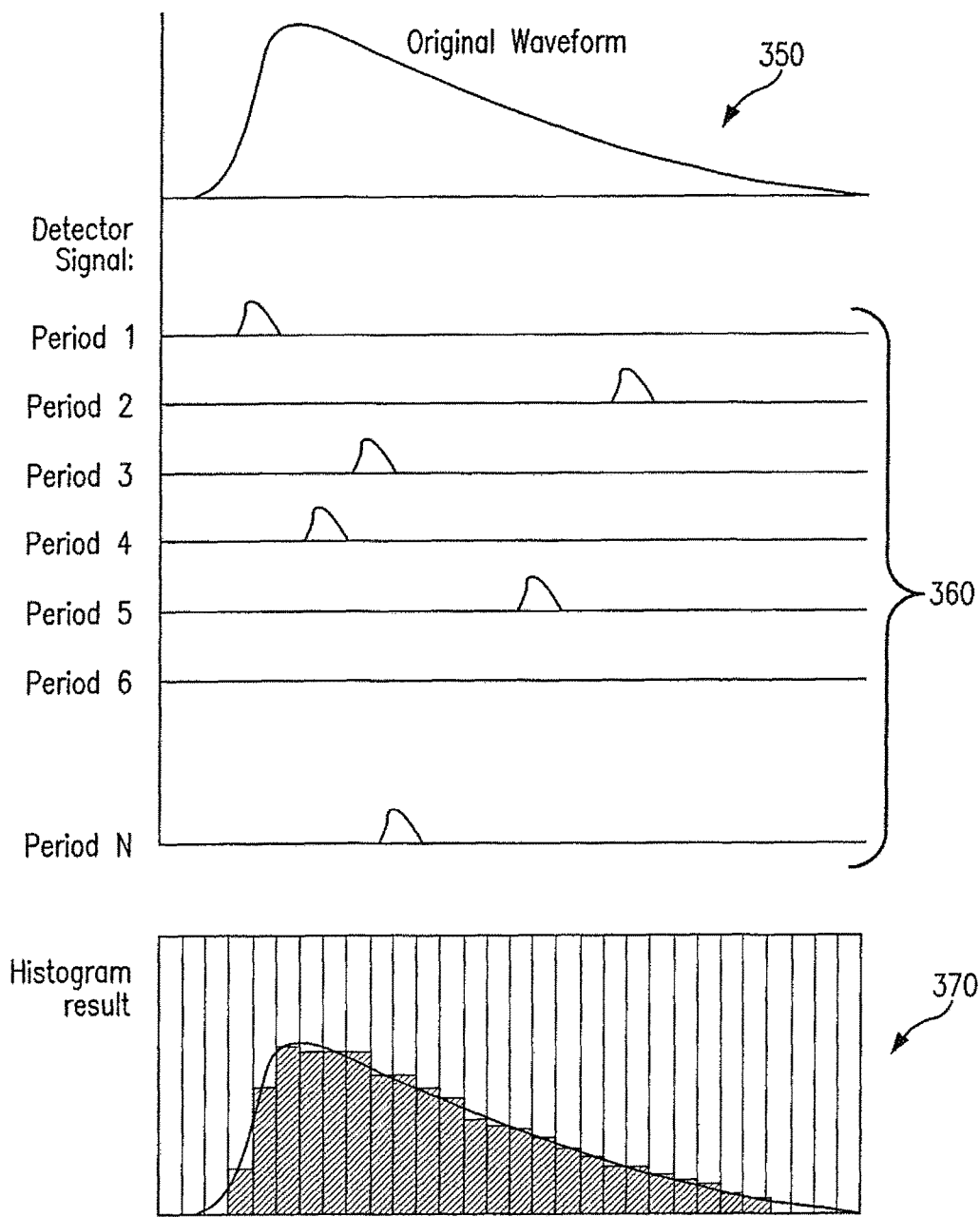
FIG. 7 is a diagram illustrating certain functions of exemplary TCSPC technology.

FIG. 7 illustrates the exemplary operation of time-correlated single photon counting (TCSPC), where a lifetime decay curve can be used in response to a discrete input pulse of light. The detector signal 350 consists of a series of randomly distributed pulses 360 due to the detection of individual incident photons. When a photon is detected, the time of the corresponding detector pulse is measured and recorded. After many photons a histogram 370 of the detection times can be produced until a smooth temporal point-spread function is generated, matching the original signal 350.

Figure 8:
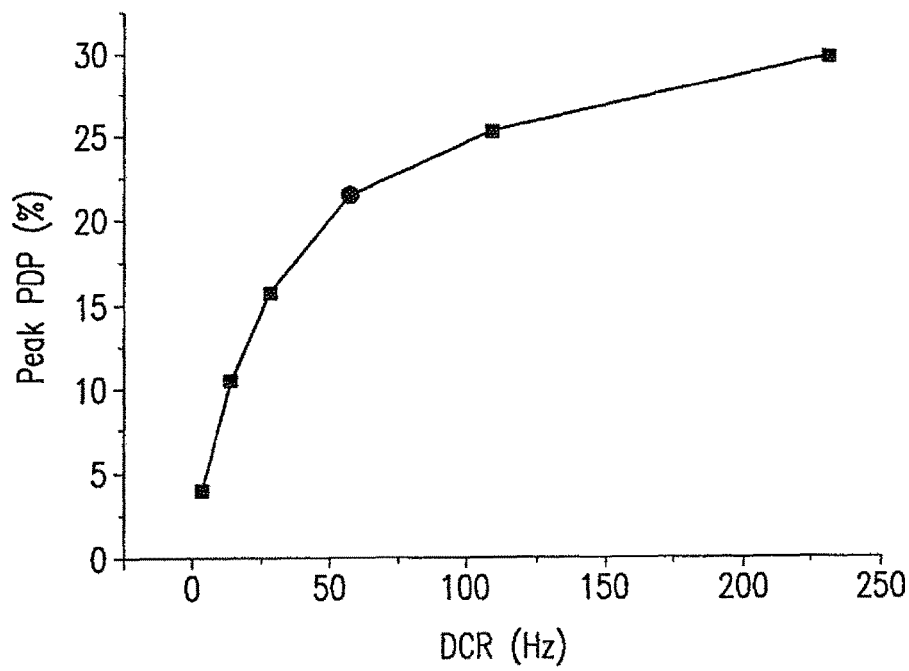
FIG. 8 is a diagram illustrating certain characteristics of the SPAD of FIG. 1

FIG. 8 shows the plot of photon detection probability (PDP) as a function of dark count rate (DCR) according to the presently disclosed subject matter. As overvoltage Vov increases, a marginal increase in PDP can be produced, which can result in a higher DCR. The red circle indicates an exemplary point of operation according to the disclosed subject matter.

Figure 9:
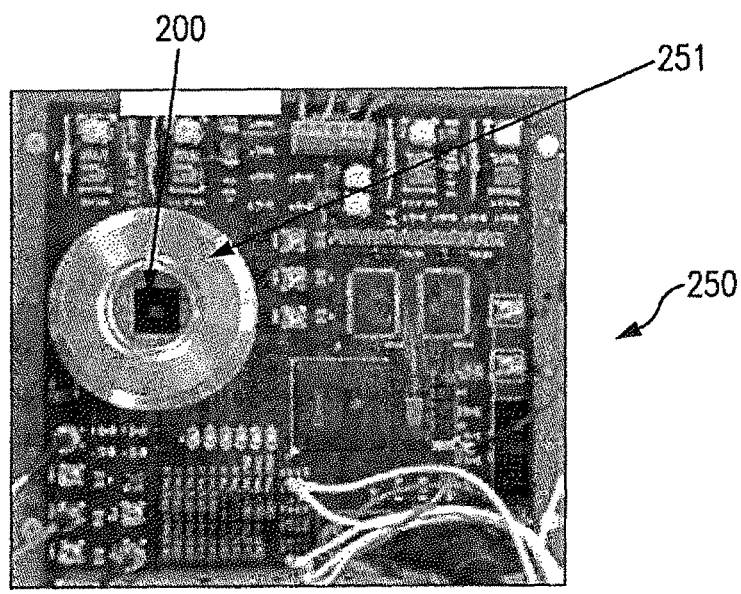
FIG. 9 is a photograph depicting an exemplary imaging apparatus according to the disclosed subject matter.

FIG. 9 shows exemplary imaging system 200 mounted on a printed circuit board 250 with a C-mount adapter 251, allowing the imager 200 to be coupled to an external microscope. Facilitated by this adapter, the camera can be mounted, for example and without limitation, in an Olympus BX51WI upright microscope with a suitable lens adaptor to provide 0.16× magnification, which can map the full field of view of the microscope onto the chip. Illumination can be provided, for example and without limitation, by a Fiantium Supercontinuum SC450-PP fiber laser, delivering pulsed light with a programmable repetition rate between 1 MHz and 20 MHz with an average power of 2 W. The imaging system can be used in any microscope system, upright or inverted, having a C-mount. The pulsed light source can be any laser that can produce pulsed light of ~10 ps and can excite the fluorophore being studied. Such lasers include, for example and without limitation, diode lasers with wavelengths of 400 nm-550 nm, or other lasers with similar pulse and wavelength ranges. According to the presently disclosed subject matter, wavelengths from 700 nm to 1000 nm can be used for two-photon imaging. Such wavelengths can be generated, for example, by a Ti:sapphire laser. The pulsed light source can include an acousto-optic tunable filter unit which can allow for selection of pulsed excitation light of a wide range of wavelengths.

Figure 10:
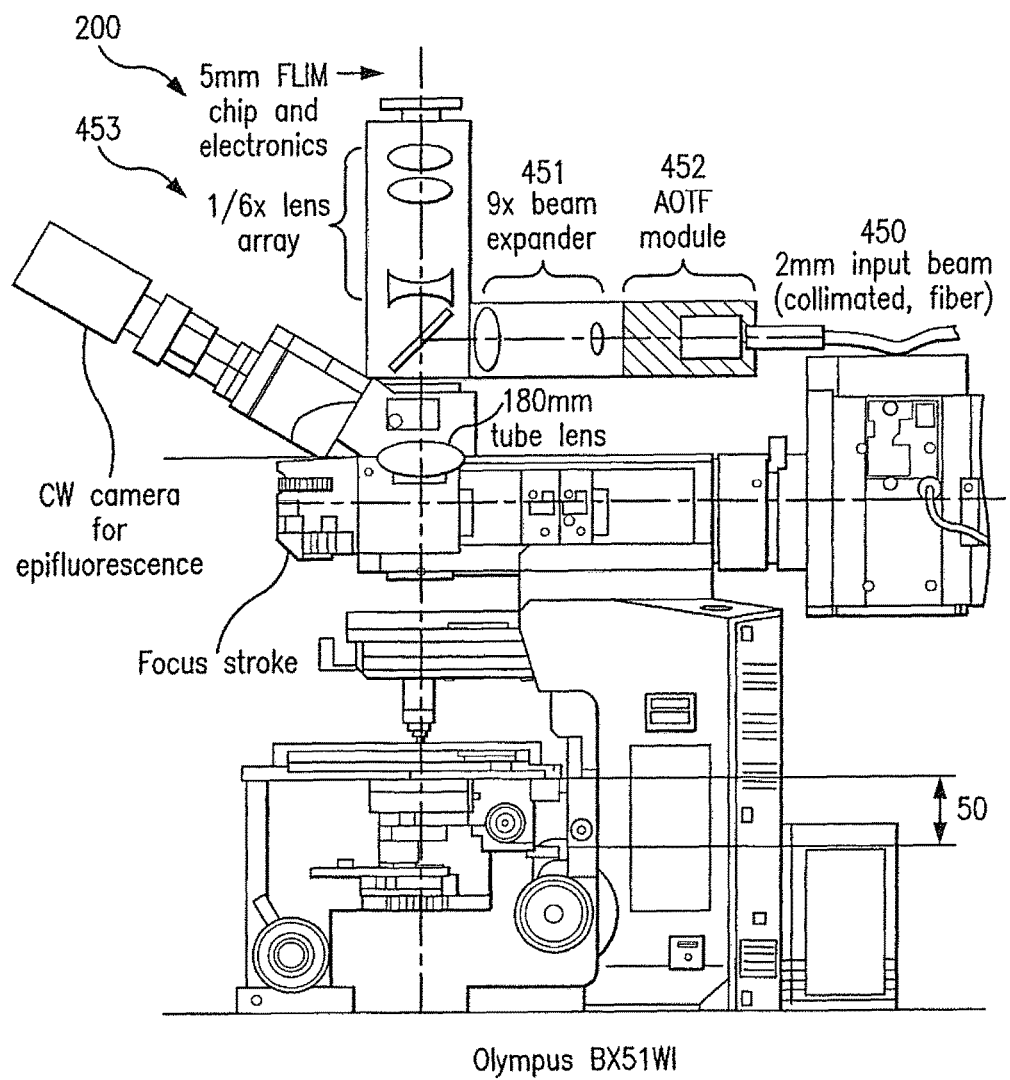
FIG. 10 is a diagram illustrating an exemplary imaging apparatus according to the disclosed subject matter

FIG. 10 illustrates an exemplary embodiment of the imaging apparatus 200 that can allow for beam expansion and collimation of a fiber-coupled laser to be incorporated into the camera-mount. The collimated input beam 450 is guided via a beam expander 451 and an AOTF module 452 that can allow for the selection of an appropriate excitation wavelength through a lens array 453 and onto a CMOS imaging array 200. This embodiment can reduce the number of optical elements, which can introduce temporal distortions into the incoming light signal, and thus improve performance.

Figure 11:
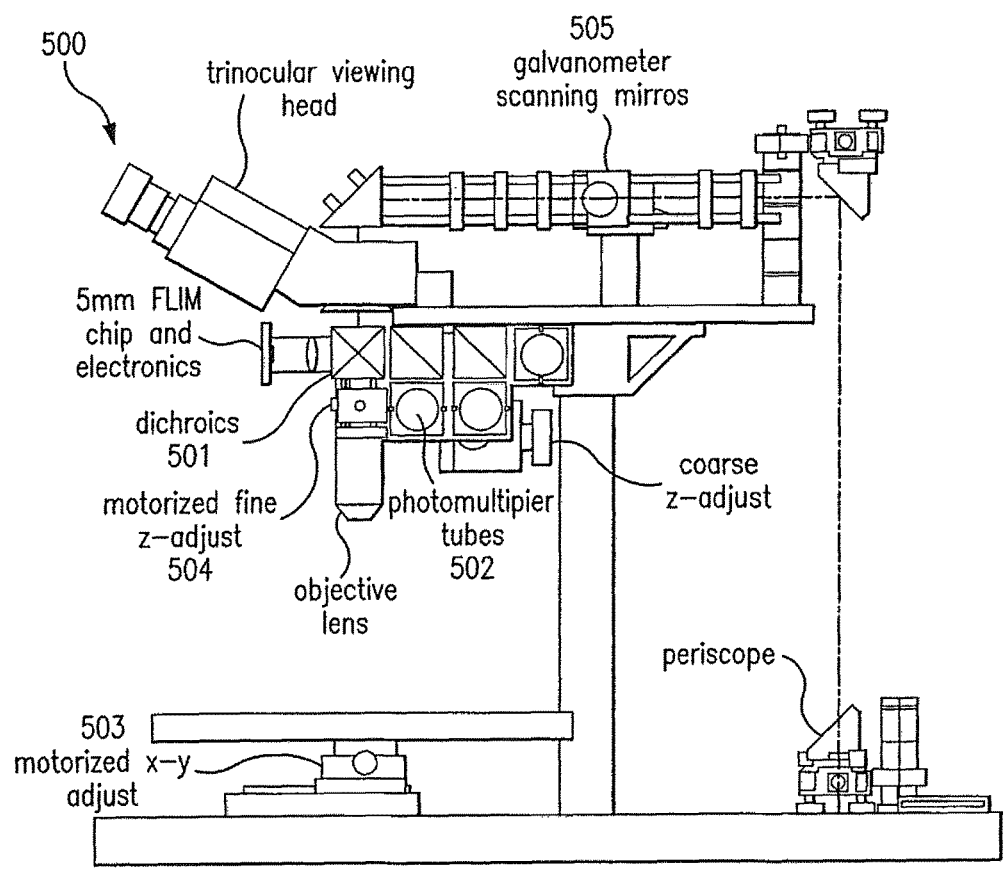
FIG. 11 is a diagram further illustrating an exemplary imaging apparatus according to the disclosed subject matter.

FIG. 11 illustrates an exemplary two-photon microscopy system utilizing the image apparatus 200 of the disclosed subject matter. Fluorescence light can be routed to the imager 200 by flipping the orientation of the system's long-pass dichroic 501, which would otherwise route light to the system's three spectrally resolved photo multiplier tubes (PMTs) 502. The system can be adjusted using motorized x-y adjusters or a fine-z adjuster 504. Data collected in this way can be reshaped into an image (e.g. 256×256 pixels), with frame rate at least partially affected by the scan rate of the system, which can be, for example, 4000 lines per second based at least in part on galvanometer mirror 505 speeds, the pixel rate of acquisition (e.g., 0.5-2 MHz), and the detection bandwidth of the system (e.g., 1-2 MHz). Frame rates of around 16 Hz can therefore be achieved.

Figure 12:
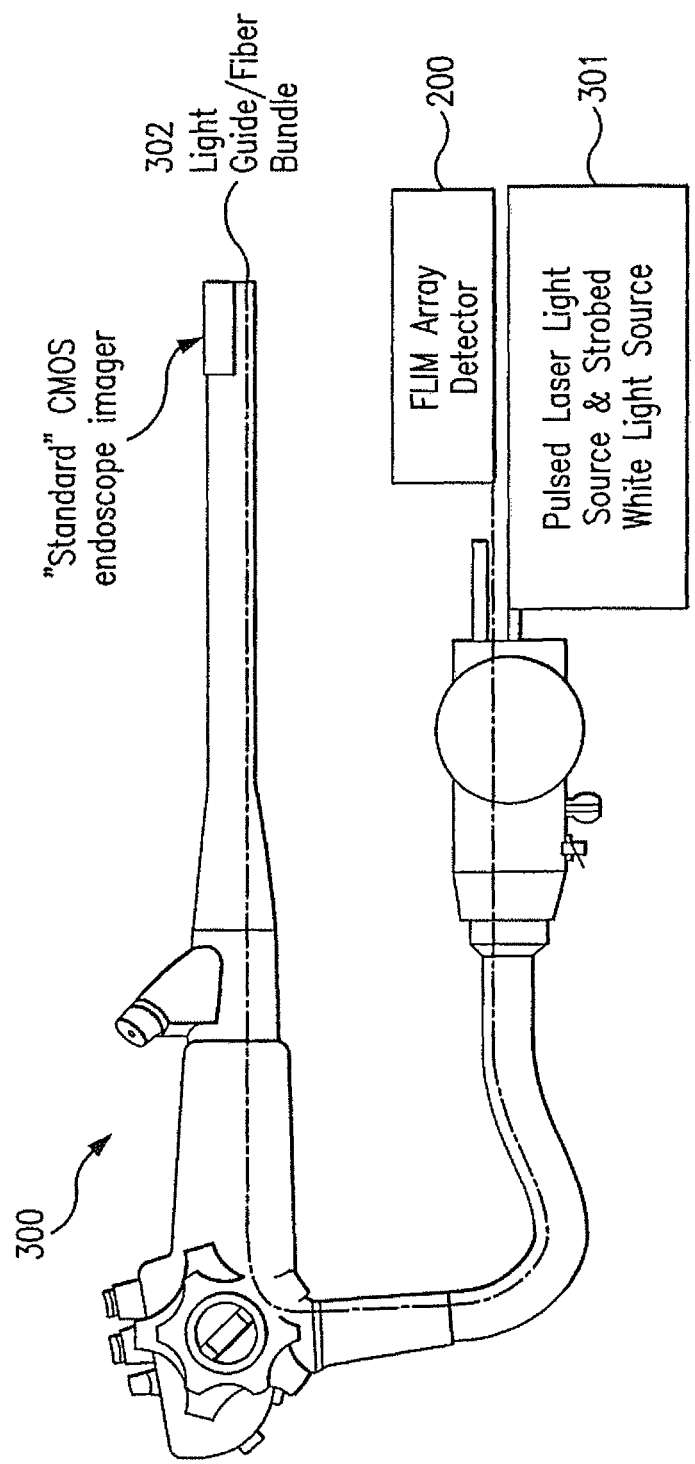
FIG. 12 is a diagram illustrating certain features of an exemplary imaging apparatus according to the disclosed subject matter.

FIG. 12 shows an exemplary embodiment of an endoscope 300. The light source 301 can produce standard white light, strobed on and off, for example, for a period of 16 ms. During the periods of darkness, the light source 301 can produce a laser pulse in order to acquire fluorescence lifetime data on the region being scanned. The pulsed laser light can be routed through the endoscope 300 and can excite a region of tissue in a wide-field mode. The fluorescence emission from the sample can be channeled back through the endoscope using a light guide or fiber bundle 302 and to the CMOS imager 200. In this manner, traditional endoscopy can be combined with FLIM techniques according to the presently disclosed subject matter.

In an alternative embodiment, an array detector, such as a camera, can be utilized. A single frame of an image can be acquired by exposing the camera while the focused beam is scanned over the whole image. Each pixel on the camera can detect the light emerging from the sample when the laser beam is scanning over that corresponding region of the sample. In this manner, the speed of the system can be improved, based at least in part on the scanning speed of the laser beam and the frame rate of the camera, which can now equal the frame rate rather than the pixel rate. In some embodiments, speed can be improved by scanning the sample with multiple beams at once, rather than collecting the signal from each point in series, as performed for example for PMT-based imaging. Increasing the number of beams scanning the tissue can increase frame rates by a factor of the number of beams. Compared to scanning FLIM, imaging multiple scanning spots onto the FLIM chip can allow for accumulation of fluorescence decays in many pixels in parallel, and can produce images at the frame rate of the chip. The disclosed subject matter can be utilized for many biological applications, at least some of which utilize more expensive and slower FLIM instrumentation.

In one example, the imager 200 disclosed herein can be used to illustrate the dynamics of voltage sensitive dyes that can use FRET mechanisms (e.g. oxonol-TRITC), which can provide changes in fluorescence lifetime. Sequences of images can be acquired at >200 Hz frame rates during stimulation of the LGN, alternating between CW epifluorescence and FLIM imaging to verify the integrity of the response in a sample slice. FRET-VSDs can be slower to respond to changes in membrane potential, so a range of other voltage sensitive dyes (Di-4-ANEPPS, RH-1691) can also exhibit fluorescence lifetime shifts. These dyes can be imaged in brain slices, and then in an in-vivo rodent brain using the two-photon FLIM system 500. For in-vivo tests, rats can be prepared by creating a 4 mm×4 mm glass cranial window over the somatosensory cortex under isoflurane anesthesia. The cortex can be stained with VSDs dyes prior to sealing the window. The rats can then be transferred to the stage of the two-photon FLIM system and imaged during hindpaw or forepaw stimulation. Calcium sensitive dyes can provide higher % signal changes, and can exhibit lifetime shifts.

Intrinsic fluorescence from NADH and FAD can also be imaged in brain slices. The protein-binding dynamics of these two metabolites can cause changes in the lifetime of the fluorescence of these molecules, and the dynamics of these changes can be used to examine cortical metabolism and metabolic insults, such as stroke. For two-dimensional wide-field imaging in brain slices, FAD can be excited using 470 nm light from a Fiantium supercontinuum laser, and fluorescence can be detected at around 530 nm. For NADH imaging, two-photon excitation at 740 nm can be used, and fluorescence can be collected at 460 nm. Each of these dyes can have a broad spectral response, which can be used to excite the fluorescent molecules, in addition to having a broad emission response once excited. The values given here represent excitation and emission wavelengths selected to improve intensity and simplify filter selection. Dynamic changes in FAD lifetime during stimulation, therefore, can be with the wide-field FLIM system. Larger changes can be invoked by reducing the oxygen saturate levels of the slice's perfusate. The two-photon system can then be used to explore both NADH and FAD fluorescence lifetime dynamics in brain slices or in-vivo.

SPAD-based CMOS camera chips can be utilized for a wide range of bioimaging applications. These chips can be integrated into, for example, two imaging platforms to allow for testing and refining of their performance, while also providing benefits to several biological applications. SPAD-based CMOS camera chips can be integrated for high-frame-rate wide-field FLIM. A multi-spot scanning two-photon microscopy configuration can be implemented for 3D, sub-micron scale FLIM imaging, which can thus be performed at frame rates of three to four orders of magnitude higher than other systems. Both of these systems can be used to characterize and improve the performance of the disclosed subject matter, for example by imaging FLIM dynamics of voltage-sensitive dyes and NADH protein binding in living brain slices.

According to another aspect of the disclosed subject matter, an exemplary 64-by-64 pixel CMOS-compatible, solid-state imager 200 capable of pixel-resolved TCSPC is provided as shown in FIG. 1. The imager 200 can be produced in a 0.35-μm CMOS process. Performance can be improved using SPADs 101 developed in a 0.13-μm CMOS process, as disclosed herein. This 0.13-μm CMOS process can allow for improved timing resolution and frame-rate performance of the imager 200 according to the disclosed subject matter. Several microscopy systems are provided, as in FIGS. 11 and 12, which can image high-speed fluorescence dynamics in living tissues, particularly in the brain.

Fluorescence microscopy can be performed using intensity measurements, with optical filters isolating the fluorophore's emission from incident excitation light. Detected intensities can vary with fluorophore concentration, as well as with light-path length, the density of intervening material and background light levels, and can attenuate over time through photobleaching. The use of ratiometric measurements can reduce these effects. However, these methods can involve in-situ calibration procedures that can be difficult to perform.

Fluorescence lifetime imaging, which can measure the rate of decay of a fluorophore instead of its intensity, can overcome many of these challenges. The lifetime of a fluorophore $\tau$ can represent the time from an impulse excitation until the emission intensity has decayed to 1/e of its peak. For fluorophores, such as many organic dyes, whose decay profiles can be mono-exponential, i.e., $I(t)=I_oe-t/\tau$, the lifetime can correspond to the average time until the emission of the first photon after excitation. Lifetimes can be on the order of a few nanoseconds. However, many fluorophores, for example in vivo, can have multi-exponential decay functions Lifetime can be considered an intrinsic property of a fluorophore, which can be dependent on its chemical composition and conformation. However, through excited-state interactions, lifetime can be affected by the fluorophore's chemical and physical environment, as well as by the proximity of other molecules through a process known as Förster resonance energy transfer (FRET) as is well known and practiced in the art.

The sensitivity of fluorescence lifetime to molecular and environmental dynamics, along with its tolerance of effects such as photobleaching, can allow for FLIM imaging to be applied to biological research. However, improved imaging speed, cost and form factor of FLIM devices is desired.

Time-resolved measurements of optical photons on the scale of ~10 ps-20 ns can be made, for example using TCSPC, frequency-domain measurements, and/or high-speed gated intensifier CCD cameras.

TCSPC can provide a full temporal point spread function, or lifetime decay curve, in response to a discrete input pulse of light. As illustrated in FIG. 2, TCPSC can serially determine the time-delay between detected single photons and a reference pulse and create a histogram of the delays of each detected photon until a smooth temporal point-spread function is generated. Frequency-domain measurements can provide a phase-shift for a given incident light modulation frequency, and thus can provide only a single measure of the group delay of photons, or an estimate of a mono-exponential lifetime. Gated intensifier cameras can use high-speed modulation of an intensifier to only detect photons arriving within a pre-defined time-gate at some delay following a trigger pulse (or some phase shift via homodyne detection in response to frequency-modulated illumination). Therefore, although a wide-field image can be produced for a particular time-window, forming a suitable point-spread function of arriving photons can involve acquiring images at multiple gate delays in sequence. Switching intensifier gate delays can be relatively slow, and generally performed sequentially, which can result in reduced temporal resolution in spite of the relatively high frame-rates of certain CCD cameras.

For conventional laser scanning FLIM microscopy, a single TCSPC detector channel can be used to collect light emerging from points serially illuminated by a focused scanning laser beam. While a single channel can be utilized, and a full temporal point spread function can be acquired for each pixel, the imaging frame rate can then be affected by the number of pixels in each image, and the dwell time utilized at each pixel to acquire the temporal profile with suitable signal to noise. This can result in FLIM fate rates of around 0.3 Hz. For wide-field fluorescence lifetime imaging with a high-speed gated intensifier camera, speed can be affected by the number of gates acquired to suitably characterize the lifetime (or temporal profile) of the detected signal.

While TCSPC approaches can be beneficial, they can also affect data acquisition rates. In situations that are not affected by photons, pulse pile-up errors can result. Certain TCPSC systems can use a laser source generating ~1 ps pulses at 40 MHz along with PMTs and associated electronics that have finite dead-times, during which a second photon can go undetected. If the detector dead-time is on the order of the laser pulse duty cycle (for example, 24 ns), incident photon fluences can be kept sufficiently low to prevent more than one photon from reaching the detector within the same duty cycle. If fluences are too high, then the TCSPC channel can be prevented from detecting photons after the first photon has arrived, and the temporal distribution recorded can be skewed towards earlier times. TCSPC implementations can therefore allow for count rates from between 0.1 to 0.01 times the repetition rate of the laser (for example, 400 kHz as embodied herein). At least 400 photons can generate a smooth temporal profile, such that the dwell time for each pixel can be configured to be at least 1 ms, and thus a 128×128 image can take over 16 seconds to acquire.

According to another aspect of the disclosed subject matter, photon-collection-limited frame rates of more than 1 kHz for a 128-by-128 imager can be provided. This can be achieved by implementing 0.13-μm CMOS circuits. Improved electronics can allow this imager 200 to achieve binning time resolution of better than 60-ps with dead times of less than 200 ps. These reduced dead-times, combined with a maximum-likelihood based statistical approach can allow the imager 200 to overcome pulse pile-up and improve frame rates and signal-to-noise, as described further herein. A comparison of certain features of the presently disclosed subject matter and other technologies is presented in Table 1.

TABLE 1

|  | Time-domain Gated CCD system | TCSPC-based FLIM system | Second-generation SPAD imager (Imager II) |
|---|---|---|---|
| Spatial Resolution | 256-by-256 | 128-by-128 | 128-by-128 |
| Dynamic range | 12 bits | 10 bits | 10 bits |
| Frame rate | 0.33 Hz | 0.03 Hz | 1 kHz |
| Temporal resolution | 100 ps | 10 ps | 60 ps |
| Effective quantum efficiency of detector | 20% | 40% | 40% |

Applications and uses of the disclosed subject matter include TCPSC-capable CMOS camera chips implemented for fluorescence lifetime imaging and microscopy; both to allow for improved camera chip design with respect to imaging hardware and software, as well as to examine biologically important targets.

Parallelization made possible by SPAD devices according to the disclosed subject matter can be utilized in various applications. For example, samples can be placed in proximity to the imager 200 in a near-field configuration, or the imager 200 can be used in a wide-field microscope or a macroscopic imaging system. Additionally or alternatively, the chip can be incorporated into a laser scanning imaging system, for example by inclusion in a multispectral time-resolved laminar optical tomography system, in a spinning disk confocal, or in a multi-beam two-photon configuration. Wide-field fluorescence lifetime imagers can provide simplicity and a wider range of lights sources, and multi-beam two-photon configurations can provide depth-resolved cellular level imaging. The imager 200 can also be incorporated in an endoscope 300 imaging system as seen in FIG. 13 and explained in detail above.

Fluorescent dyes can be used as markers to allow visualization of biological processes and analytes. In-vitro, fluorescent dyes can be used extensively as labels for proteins and DNA in immunoassays and microarray applications. However, in intact cells and tissues, and even in vivo, fluorescent labeling and transgenic expression approaches can be used to evaluate real-time function and physiology. Three-dimensional multi-photon microscopy can be utilized in-vivo, which can allow biologists to capture the dynamics of functioning intact organs. However, dynamic imaging of fluorescence lifetime contrast can be affected by FLIM imaging speeds.

FRET-based assays can also be utilized for biological research. A FRET pair can include a donor and acceptor molecule, the former of which can emit fluorescent light within the excitation band of the latter. If two such molecules are closer together than around r=10 nm, the two molecules can exchange energy non-radiatively, which can occur as a function of 1/r6. As such, a sample can be illuminated with light that excites only the donor molecule, and the two molecules can be very close together, and thus the sample can emit less light at the donor emission wavelength and more light at the acceptor emission wavelength. The relatively short distances at which FRET occurs can correspond to the proximity required for two molecules (e.g. proteins) to bind, and thus molecules of interest can be tagged with fluorophores, and their molecular interactions over distances below the resolution limits of certain imaging techniques can be evaluated.

Small changes in intensity can be desired, which can be affected by changes in dye concentration and photobleaching. Nevertheless, FRET can affect the fluorescence lifetime of the donor molecule, at least in part because energy can be non-radiatively lost from the molecule while being emitted radiatively, thus shortening the lifetime. FLIM can be a sensitive and robust method to detect FRET.

Active dyes can be utilized as fluorescent markers to report changes in their local environment, such as calcium concentration, pH or membrane potential, with changes in their fluorescent properties, including spectral shifts and changes in intensity. Many of these contrast agents can utilize the effects of FRET, although others can utilize electrochromic effects or undergo direct conformational changes. Such active dyes can therefore exhibit changes in fluorescence lifetime in response to their environment.

Many kinds of voltage sensitive dyes (VSDs) can be utilized in neuroscience and cardiac research. Many VSDs can utilize electrochromic effects that respond quickly enough to reveal the dynamics of single action potentials. For purpose of comparison, calcium sensitive dyes can have a slower response, for example 100-200 ms. However, the use of VSDs for cellular-level microscopy can present challenges, for example related to low signal changes (~0.15%) due at least in part to high background levels of fluorescence. By imaging changes in fluorescence lifetime at speeds nearing 1 kHz, active dyes can offer fluorescence lifetime contrast for high-speed measurements of action potentials at the cellular level.

The presence of intrinsic fluorophores, including NADH, flavoproteins, keratin, elastin, retinols, tryptophan, porphyrins and collagen cross-links, can be found in structural elements of living tissues, as well as operate in metabolic pathways.

Fluorescence lifetime measurements can reveal improved contrast over measurements of fluorescence intensity alone. For example, the fluorescent lifetimes of metabolites NADH and flavin adenine dinucleotide (FAD) can change depending on their cellular environment, including whether they are free or protein-bound. In turn, this bound or un-bound state can be correlated with the health of the cell, with changes seen in precancerous cells, and cells undergoing apoptosis and necrosis. Intrinsic lifetime contrast therefore can be utilized to delineate diseased tissues from normal tissues or cells.

Lifetime measurements can be independent of photobleaching and the overall detected fluorescence intensity. Furthermore, many areas of biological research can be improved by the availability of high-speed, real-time FLIM imaging technology.

The foregoing merely illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody its principles and are thus within its spirit and scope.

What is claimed is:

1. A single-photon avalanche diode comprising:
   a central junction including a central p+ area and a deep-n well in contact with the central p+ area;
   a p-type guard ring disposed between the central junction and the deep-n well, at least partially in contact with the central junction; and
   a plurality of shallow trench isolations separated from the central p+ area, wherein the p-type guard ring is in contact with a single shallow trench isolation from the plurality of shallow trench isolations proximal to the central junction.

2. The single-photon avalanche diode of claim 1, further comprising a photosensitive area disposed proximate to the surface of the diode.

3. The single-photon avalanche diode of claim 2, wherein the photosensitive area has an octagonal shape.

4. The single-photon avalanche diode of claim 1, wherein the guard ring is configured to substantially surround the p+ area.

5. The single-photon avalanche diode of claim 1, wherein the guard ring is disposed between the p+ area and the shallow trench isolation.

6. The single-photon avalanche diode of claim 5, wherein the guard ring is adjacent the p+ area and the shallow trench isolation.

7. An imaging apparatus, comprising:
a plurality of pixels, each pixel comprising:
a complementary metal-oxide-semiconductor-implemented single photon avalanche diode, the single photon avalanche diode comprising
a central junction including a central p+ area and a deep-n well in contact with the central p+ area,
a p-type guard ring disposed between the central junction and the deep-n well, at least partially in contact with the central junction, and
a plurality of shallow trench isolations separated from the central p+ area, wherein the p-type guard ring is in contact with a single shallow trench isolation from the plurality of shallow trench isolations proximal to the central junction; and
one or more signal converters electrically coupled to the diode and configured to detect changes in output therefrom.

8. The apparatus of claim 7, wherein the one or more signal converters comprise delay-locked loop-based time-to-digital converters.

9. The apparatus of claim 7, each single photon avalanche diode further comprising a quenching circuit and a resetting circuit connected in series with the single photon avalanche diode.

10. The apparatus of claim 9, wherein the quenching circuit further comprises a resistive component.

11. The apparatus of claim 10, wherein the resistive component further comprises a variable resistor.

12. The apparatus of claim 10, wherein the resistive component further comprises a resistor.

13. The apparatus of claim 9, wherein the single photon avalanche diodes are arranged in an array.

14. The apparatus of claim 13, wherein the array further comprises a two-dimensional 64 * 64 array.

15. The apparatus of claim 13, wherein the array further comprises a two-dimensional 128 * 128 array.

16. The apparatus of claim 9, wherein the signal converters are further coupled to a processor configured to compress data.

17. The apparatus of claim 9, wherein the apparatus is configured to detect a signal categorized as a non-homogeneous Poisson process.

18. The apparatus of claim 9, further comprising a C-mount adapter disposed proximate to the surface of the apparatus, enabling it to connect to a microscope.

19. The apparatus of claim 7, wherein the resetting circuit further comprises an active resetting circuit.

20. A laser scanning microscopy system comprising the imaging apparatus of claim 7.

21. A two-photon microscopy system comprising the imaging apparatus of claim 7.

22. An endoscopic imaging system comprising the imaging apparatus of claim 7.

* * * * *